United States Patent [19]

Hideshima

[11] Patent Number: 5,270,924
[45] Date of Patent: Dec. 14, 1993

[54] OPHTHALMOLOGICAL IMAGE PROCESSOR

[75] Inventor: Masayuki Hideshima, Tokyo, Japan

[73] Assignee: Kabushiki Kaisha Topcon, Tokyo, Japan

[21] Appl. No.: 798,081

[22] Filed: Nov. 27, 1991

[30] Foreign Application Priority Data

Nov. 30, 1990 [JP] Japan ................. 2-335947

[51] Int. Cl.$^5$ .............................................. G06F 15/00
[52] U.S. Cl. ........................................ 364/413.13
[58] Field of Search ............. 364/413.13; 382/2, 6, 382/54; 351/205, 206, 211

[56] References Cited

U.S. PATENT DOCUMENTS

| | | | |
|---|---|---|---|
| 4,109,237 | 8/1978 | Hill | 382/2 |
| 4,494,838 | 1/1985 | Wallquist et al. | 351/206 |
| 4,891,757 | 1/1990 | Shroy, Jr. et al. | 364/413.13 |
| 4,908,876 | 3/1990 | DeForest et al. | 382/54 |

Primary Examiner—Roy N. Envall, Jr.
Assistant Examiner—Ari M. Bai
Attorney, Agent, or Firm—Finnegan, Henderson, Farabow, Garrett & Dunner

[57] ABSTRACT

The fundus image processor of this invention comprises an image inputting means including a fundus camera for inputting electronic images of a subject's eye, video camera, magnetic disk apparatus and still video apparatus. Further, this apparatus also comprises a display means for displaying the fundus image input by the image inputting means. Further, the apparatus also comprises an image identification/processing means for identifying the state of the image input by the inputting means from the positions of light and dark regions on the image, and causes the results of this identification to be displayed on the display means.

14 Claims, 8 Drawing Sheets

OPHTHALMOLOGICAL IMAGE PROCESSOR

BACKGROUND OF THE INVENTION

1. Field of the Invention

This invention concerns a fundus image processor for electronic inputting and processing of fundus images.

2. Description of the Prior Art

In recent years, there has been a tendency to replace photographs taken on silver halide film by electronic images. This is true not only in the ophthalmological field, but also where electronic images offer particular advantages such as periodic health check-ups or for examining the three-dimensional structure of a fundus. Electronic images are thus making progressive inroads, initially in those fields where it would be difficult to perform the task at hand without them.

However, at the current time, electronic image processing systems which are economically competitive give poorer images than silver halide photographs. In those fields which require accurate diagnosis, one way of dealing with this problem would be to take a silver halide photograph on film, and convert it to an electronic image for storage purposes.

In group health check-ups and other situations wherein extreme precision is not required, an electronic image of the fundus could be obtained directly and used as it is. In such a case, if all the images were electronic images, comparisons could be made with previous images. However, many of the records are still on silver halide film, and it is necessary to convert earlier images to electronic images with the aid of a video camera or a linear scanner.

The need for this type of conversion may be expected to continue for some time. As the operator must take care to distinguish between the front, back, top and bottom of a slide film, and between images for the left and right eye, however, the procedure is troublesome, and it sometimes led to the inputting of incorrect images.

SUMMARY OF THE INVENTION

It is therefore an object of this invention to provide a fundus image processor which, in order to avoid this kind of trouble, can automatically distinguish between the front, back, top and bottom of an image, and between images for the left and right eye.

To achieve the aforesaid object, the fundus image processor of this invention comprises image inputting means for inputting an electronic image of a subject's eye, display means for displaying the image of a subject's eye input by the inputting means, and image distinguishing/processing means for distinguishing the state of the image input by the inputting means from the positions of light and dark areas, and displaying the result on the display means.

It is a further object of this invention to provide a fundus image processor which can not only automatically distinguish between the front, back, top and bottom of an image, and between images for the left and right eye, but which, if the left, right, front and back of a fundus image are confused when an image is input, issues a warning to the operator or converts image position data read by a photographic image reader to correct image position data.

To achieve the aforesaid object, the image inputting means is a photographic image reader which can read a fundus image bearing a mark to distinguish left, right, front and back, and if left, right, front or back of a fundus image are confused when the image is read by the photographic image reader, the distinguishing means issues a warning to the operator.

Further, if left, right, front or back of a fundus image are confused when the image is read by the photographic image reader, the distinguishing means performs a coordinate transformation such that image position data which are input incorrectly are converted to correct image position data.

These and other objects, features and advantages of the present invention will be well appreciated upon reading of the following description of the invention when taken in conjunction with the attached drawings with understanding that some modifications, variations and changes of the same could be made by the skilled person in the art to which the invention pertains without departing from the spirit of the invention or the scope of the claims appended thereto.

BRIEF DESCRIPTION OF THE ATTACHED DRAWINGS

FIG. 3(a, (b) are schematic diagrams showing fundus images photographed by the fundus camera illustrated in FIG. 1.

FIG. 10(a) and FIG. 11(b) are lateral views of FIG. 10(a) and FIG. 11(a).

FIG. 12(a), FIG. 12(b), FIG. 13(a) and FIG. 13(b) are schematic diagrams for the purpose of judging left, right, top, bottom, front and back of a fundus image read from a photograph or the like.

FIG. 14(a) and (b) are schematic diagrams illustrating another example of a mark for the purpose of judging left, right, top, bottom, front and back of a fundus image read from a photograph or the like.

FIG. 20(a) and (b) are schematic diagrams for the purpose of judging the correct identity of left and right when the image file of FIG. 19 is recorded and held in a frame memory.

DESCRIPTION OF THE PREFERRED EMBODIMENTS

One embodiment of the invention will now be described with reference to the drawings.

Figure 1:
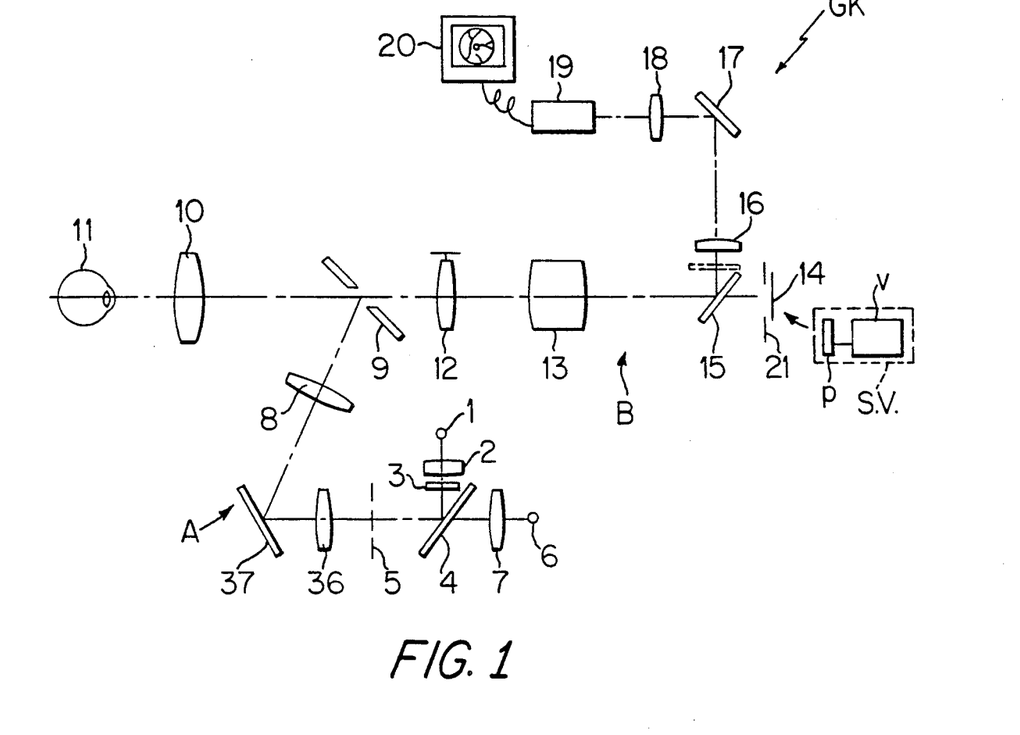
FIG. 1 is a schematic diagram illustrating one example of the optical system of the fundus camera.

FIG. 1 shows an example of the main parts of the optical system of a fundus camera GK (photographic means) for taking a photograph of a fundus image according to this invention. This fundus camera comprises an illuminating system A for illuminating a fundus of a subject and an observation system B for observing or photographing the fundus of the subject, and it is also used as an image inputting means.

ILLUMINATING SYSTEM A

The illuminating system A comprises an observation light source 1. The light beam from this observation light source 1 passes through a condensing lens 2 and an infrared filter 3 which cuts out visible light and transmits only infrared light, and is reflected by an oblique half mirror 4 to illuminate the annular diaphragm 5.

The illuminating system A also has a photographic light source 6. The light from this photographic light source 6 passes through a condensing lens 7 and the half mirror 4 so as to illuminate the annular diaphragm 5.

The light that has passed through this annular diaphragm 5 passes through a relay lens 36, oblique mirror 37 and relay lens 8 to reach a holed mirror 9 set obliquely on the optic axis of an objective lens 10, is reflected in the direction of the objective lens 10 by the holed mirror 9, and passes through the objective lens 10 to illuminate the fundus of a subject's eye 10.

PHOTOGRAPHIC SYSTEM B

The light beam reflected by the fundus of the subject's eye passes through the objective lens 10 and the aperture of the holed mirror 9, proceeds along the optic axis of the objective lens 10, and is made to form an image on a film 14 by a focusing lens 12 and imaging lens 13.

A mirror 15 is disposed in front of the film 14 such that it can be freely retracted. When making observations, it occupies the position shown by the solid line, and when taking photographs it is withdrawn to the position shown by the broken line.

When making observations, the light beam from the fundus is reflected by the upper half of the mirror 15 so as to form a fundus image on a field lens 16. The fundus image formed on the field lens is relayed to and is made to form an image on the photoelectric surface of an infrared image pickup tube 19 by an oblique mirror 17 and relay lens 18. The electrical signal from the image pickup tube is displayed as a visible fundus image on the screen of a monitor television 20.

Figure 2:
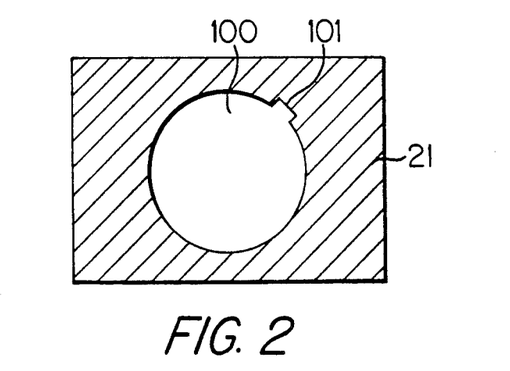
FIG. 2 is a schematic diagram showing the visual field diaphragm of FIG. 1.

A field diaphragm 21 is disposed immediately in front of a film 14 to control the shape of the field on the film. FIG. 2 shows an example of this field diaphragm 21. This field diaphragm has a circular aperture 100, and one part also has a notch 101. The operator normally distinguishes the front and back of a photograph from the orientation of this notch 101.

Herein, an example has been described where the film 14 of a 35 mm camera, not shown, is disposed immediately behind the field diaphragm 21, but an area CCD (charge coupling device) P of a still video apparatus (S.V.) (photographic means) may also be thus disposed instead of the film 14 of a 35 mm camera. In this case, a fundus image picked up by this area CCD P is recorded on the video floppy of a magnetic recording apparatus V. The image signal from this area CCD P can also be directly input to a frame memory 206 of FIG. 5.

Figure 3A:
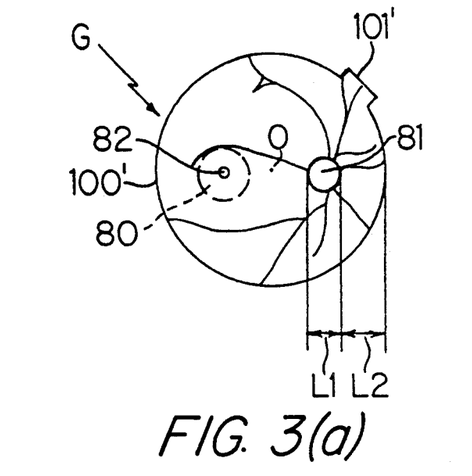
Figure 3B:
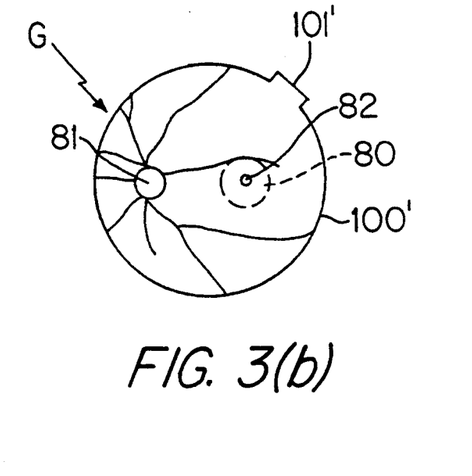

FIG. 3(a), (b) respectively show examples of fundus images of the left eye (a) and right eye (b). If this fundus image G is to be obtained at a camera angle of 45° which is widely used in health check-ups, the photographic range L2 on the side of the subject's nose is generally arranged to be 1.5 times the diameter L1 of the papilla 81. The center of the field of vision 0 is then situated between a yellow striated area or macula lutea 80 which has a relatively low reflectance, is dark and has a center hollow or center pit or fovea centralis 82, and the papilla 81 of the optic nerve which has the highest reflectance and is the brightest area of the fundus. The fundus image G also comprises a circular part 100' corresponding to the circular aperture 100 of the field diaphragm 21 and a notch 101' corresponding to the notch 101 of the field diaphragm 21.

Figure 4:
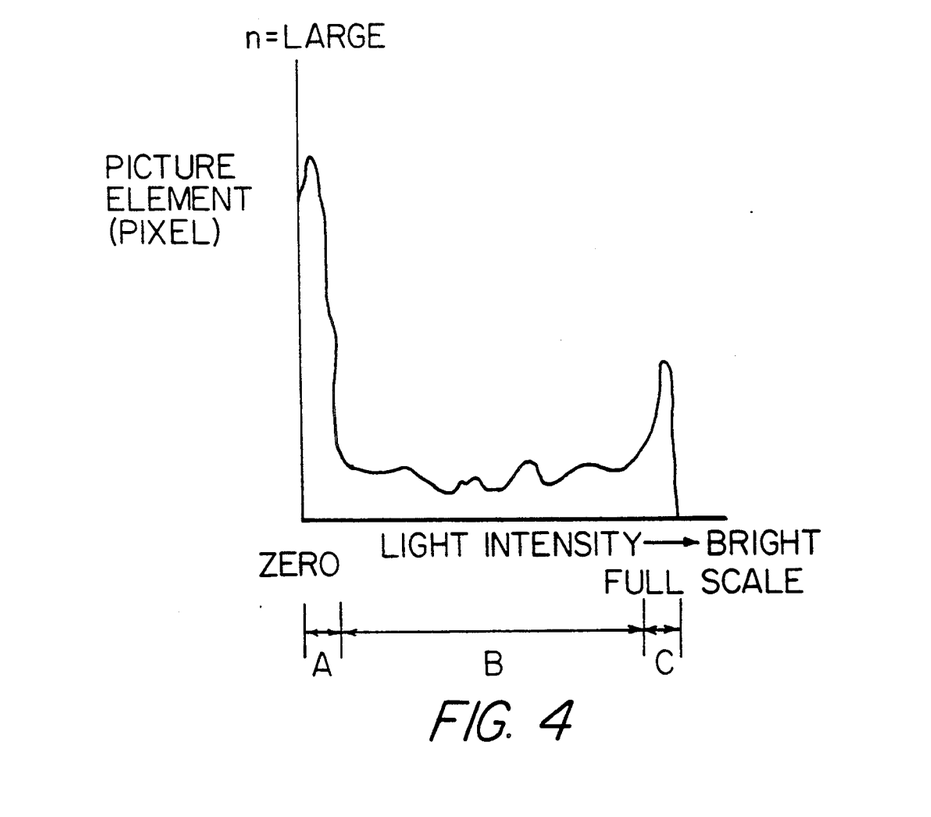
FIG. 4 is a histogram of picture elements versus light intensity of the fundus images shown in FIG. 3(a), (b).

When the fundus image having the aforesaid characteristics is converted to an electronic signal, a histogram having a number of picture elements corresponding to the light intensity is obtained as shown in FIG. 4.

In FIG. 4, the interval A corresponds to the area covered by the mask of FIG. 2, the interval C corresponds to the very bright area of the optic nerve papilla 81, and the interval B corresponds to other parts of the fundus which have an intermediate brightness.

In view of the above characteristics, it is easy to distinguish the part covered by the field diaphragm 21 and the part where there is an image, and the orientation of the notch 101 can be determined by processing the image. From the orientation of the notch, it is possible to determine whether the image is that of the left or right eye. Further, if the center 0 of the aperture 100 of the field diaphragm 21 can be located, it is possible to determine whether the image is that of the left or right eye by examining whether the optic nerve papilla 81 is on the right or left of the center 0. Further, it is possible to determine whether the image is that of the left or right eye by determining which side, i.e. left or right, is the brighter.

An example of an electronic filing apparatus FS for filing fundus images which takes account of the above points, will now be described with reference to FIG. 5.

Figure 5:
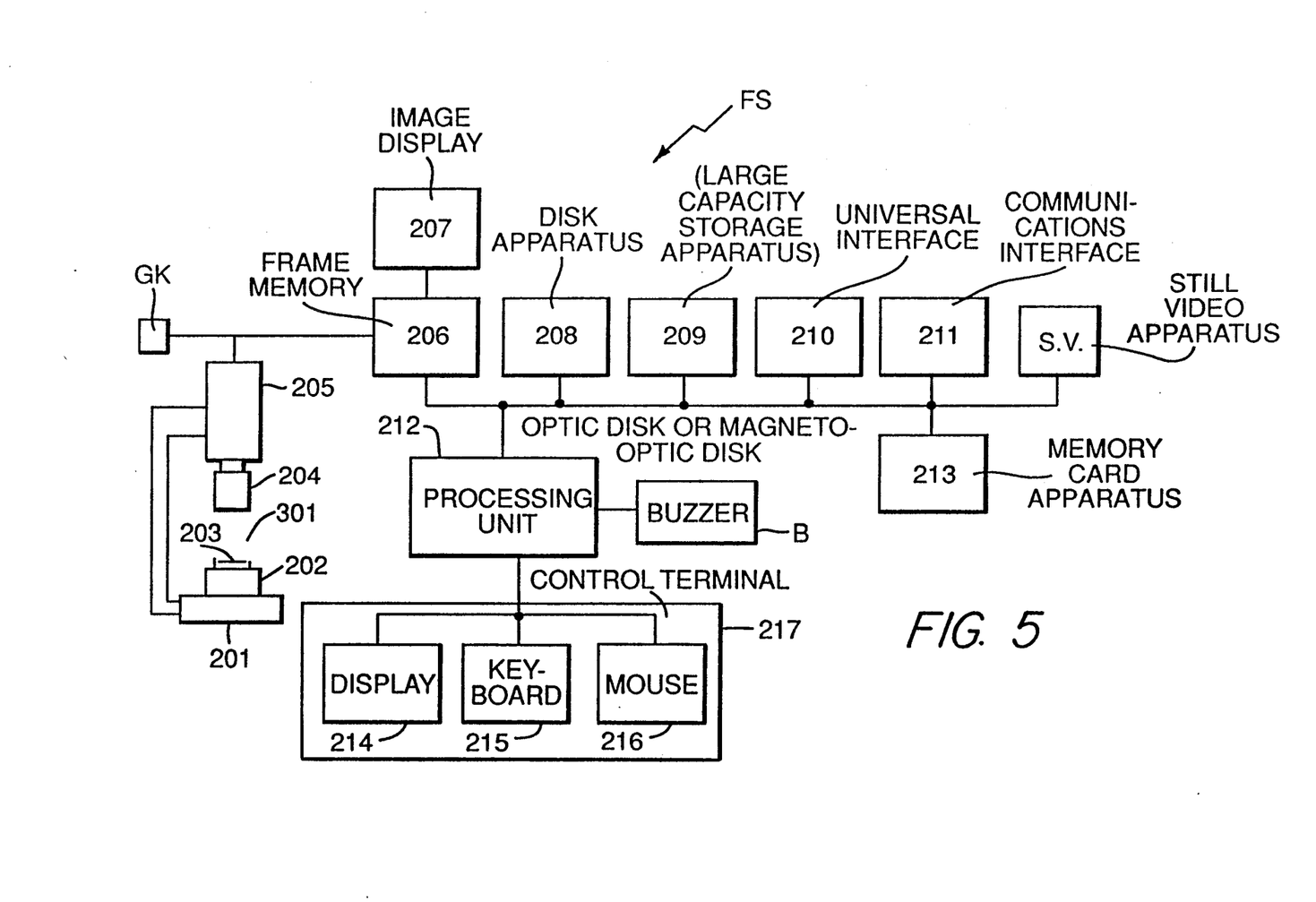
FIG. 5 shows a typical block diagram of a filing system according to this invention.

FIG. 5 shows a case where an image is input from a slide using a video camera, and a microcomputer is used as an image processor and filing controller.

This filing apparatus comprises a platform 201, a light box 202 mounted on the platform 201, and a video camera 205 (photographic means) disposed at a certain height above the light box 202 for inputting images. A holder 301 for holding a slide 203 is provided in this illuminating apparatus 202, the image on the slide held in this holder 301 being picked up by the video camera 205 through a lens 204.

Figure 10A:
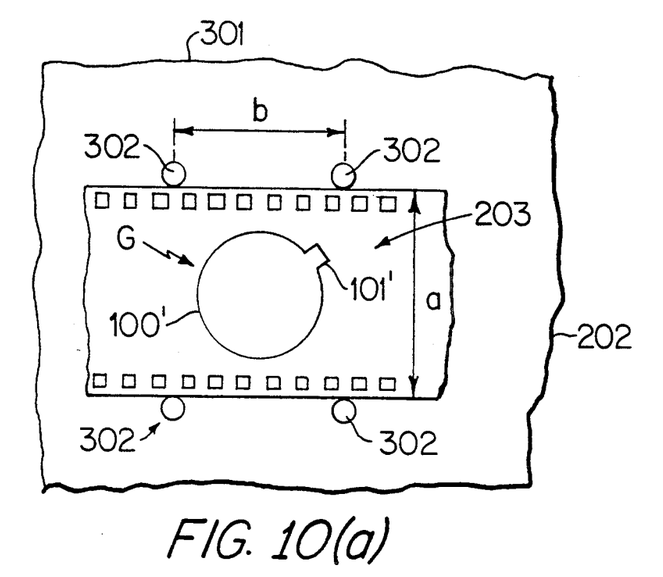
FIG. 10(a) and FIG. 11(a) are schematic diagrams illustrating one example of a holder for determining photographic position installed on a light box.
Figure 10B:
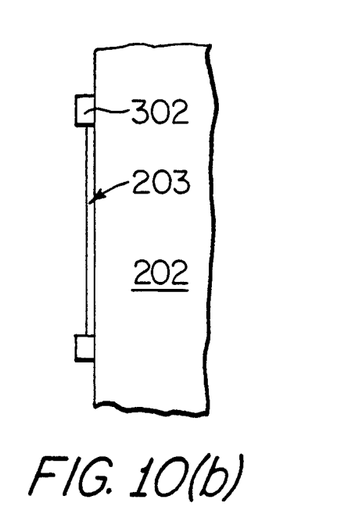

FIG. 10 shows an example of the holder 301. This example shows a case where a 35 mm film is used as the slide 203. Four pins 302 are provided in the aforesaid light box 202 so as to hold the slide 203.

In this example, the film is prevented from being incorrectly installed with a 90° rotation by making the distance b between pins in the longitudinal direction of the film, less than the width of the film a. Further, a cover glass or frame may also be used to maintain the film perfectly flat if necessary.

Figure 11A:
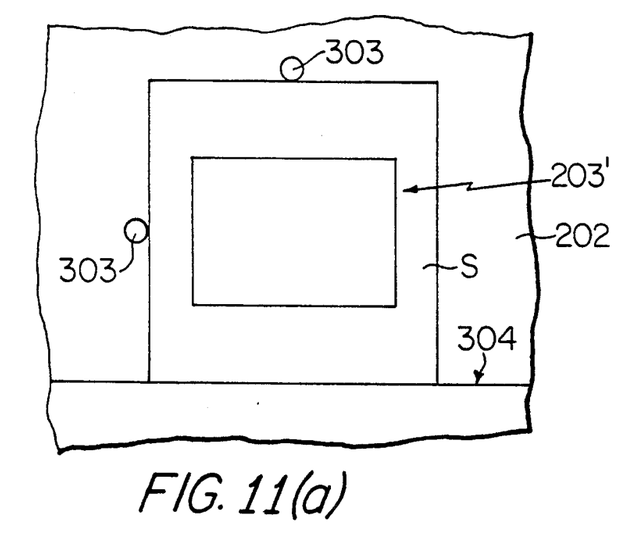
Figure 11B:
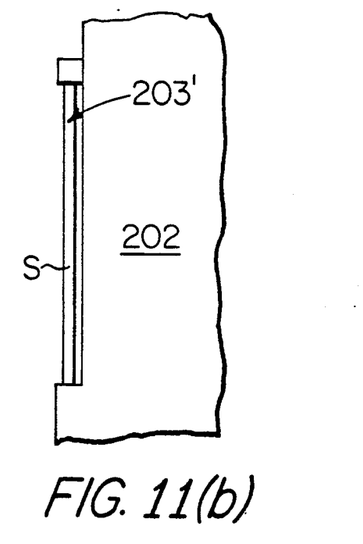

FIG. 11 shows an example wherein a slide member comprising a slide 203' mounted in a slide frame S is held by the holder. In this example, the slide mounted by a step piece 304 and a pin 303 is held in a predetermined position.

According to the aforesaid method, the slide is always held in a fixed position. This eliminates the trouble of re-aligning the slide every time it is replaced. At the same time, the slide can only be rotated 90° at a time which is a prerequisite condition for later determining whether or not front/back, top/bottom and left/right of the slide are in the correct positions.

The image signal is input to a frame memory 206 having an image display 207 for displaying its contents, and is digitized and converted to an electronic signal. The contents of the frame memory 206 are then processed by a central processing unit 212 (determining means). As described hereinafter, the central processing unit 212 functions as a means to determine the position of the image, to perform coordinate transformations, or to determine left/right, top/bottom and front/back of the fundus image, and it is therefore provided with a control terminal 217 comprising a display 214, keyboard 215 and mouse 216 (pointing apparatus).

A disk apparatus 208 for storing programs of the central processing unit 212 or temporarily storing image data (image inputting means), and a large capacity storage apparatus 209 comprising an optical disk or magneto-optic disk for permanently storing image data or a data base (image inputting means), are connected to the central processing unit 212. Further, a universal interface 210 for inputting signals from or outputting signals to external devices, a communications interface 211 for communicating with external devices, a memory card apparatus 213 for transferring small amounts of image data or data bases (image inputting means), a warning buzzer B (warning means) and a still video reader (image inputting means) are also connected to the central processing unit 212.

The action of this equipment will now be described.

The slide image 203 illuminated by the illuminating device 202. is picked up by the lens 204 and video camera 205, and temporarily stored in the frame memory 206. The video camera 205 and frame memory 206 form a photographic image reader. First, the front and back of the slide are distinguished.

This processing such as distinguishing front and back is performed on the image in the frame memory 206 by the central processing unit 212.

Figure 6A:
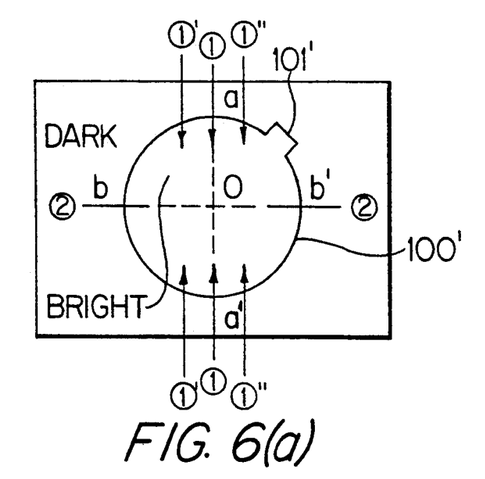
FIG. 6(a) is a schematic diagram illustrating one example of a fundus image.
Figure 6B:
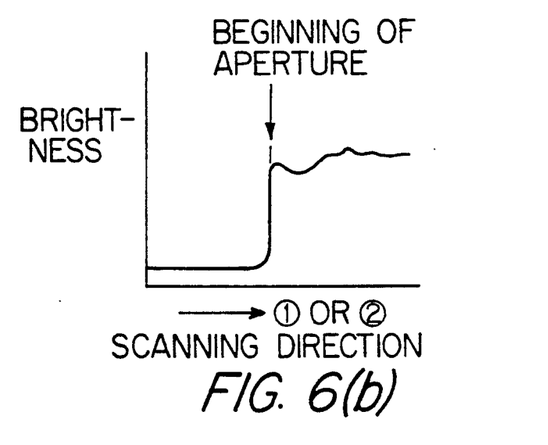
FIG. 6(b) is a schematic diagram showing the variation of brightness when the fundus image of FIG. 6(a) is scanned.
Figure 8:
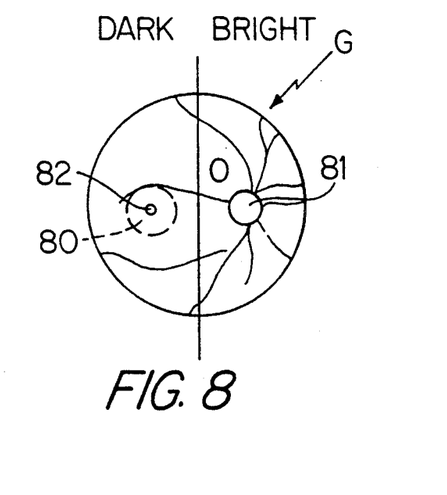
FIG. 8 and FIG. 9 are schematic diagrams for judging the correct identity of left and right fundus images.

As the aperture 100 of the field diaphragm 21 is known to be circular, it is possible to determine that the position where the image suddenly becomes brighter, such as the point t in FIG. 8(b) when the image is scanned in directions "" and "" in FIG. 6(a), is the beginning of the aperture 100.

First, the directions "501 " and "" are scanned in order to determine a top/bottom distance a, a'. If the distance a, a' is too small, the image may have been scanned when it was displaced to the left or right, so it is then scanned in the directions "", "" and the larger distance a, a' is taken. Next, the image is scanned in the direction "" at a position intermediate between the top and bottom in order to determine points b, b' in the same way.

From the coordinates a, a', b, b', the position of the center O of the aperture is found. Further, the distance b, b' is equal to the diameter of the aperture.

Figure 7:
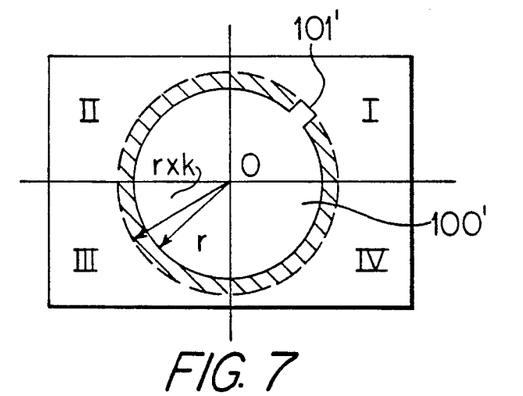
FIG. 7 is a schematic diagram for finding the position of a mark on the fundus image of FIG. 6.

Next, an average brightness is found for each quadrant of the image having a radius r extending from the center O of the aperture 100 within a range (radius r) x (predetermined constant k), i.e. within the range shown in FIG. 7. The average brightness within the aforesaid range for the quadrant containing the notch 101 is brighter than for other image quadrants.

In the example of FIG. 7, the quadrant I is brighter than other quadrants. The aforesaid procedure therefore shows that the notch 101 is present in the quadrant having the greatest average brightness.

The quadrant and shape of the notch 101 are fixed depending on the manufacturer of the equipment. If this information is preset, therefore, it is possible to determine by comparison with the information whether front/back, top/bottom and left/right of an image have been input correctly. The constant k should preferably be chosen such that whole of the notch just lies within a range r x k, and k can be determined from the set information concerning the notch.

If the detected orientation of the notch is incorrect, the apparatus issues a warning by means of the buzzer B, and a warning that the orientation is incorrect is also displayed on the display 207.

Next, the procedure for distinguishing the left and right eye will be described.

Figure 9:
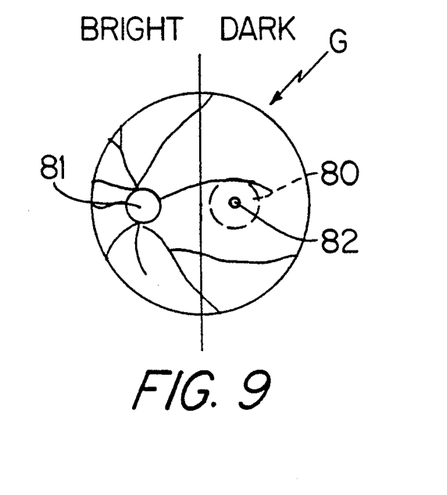

In a fundus photograph of the type generally obtained in a group health examination, there is a very bright papilla 81 on the fundus on the nose side of the visual center as shown in FIG. 8 (left eye) and FIG. 9 (right eye). In this type of fundus photograph, therefore, by determining the total light amount respectively to the left and right of the center of the visual field excluding the notch 101 of the visual field diaphragm, it is possible to know whether the image is that of the left or right eye. The total light amount can be found by summing all picture elements within the aforesaid ranges. Further, for greater speed and convenience, the number of picture elements summed in the center of the optic nerve papilla 81 can be reduced provided that a sufficient number of sampling points are obtained.

When handling an original image 203' which is mounted as shown in FIG. 11, the present orientation of the image 203' can be determined if it is known from the aforesaid procedure "in which quadrant the notch is correctly positioned", since the notch cannot be mistakenly positioned at 80° to this position.

Figure 12A:
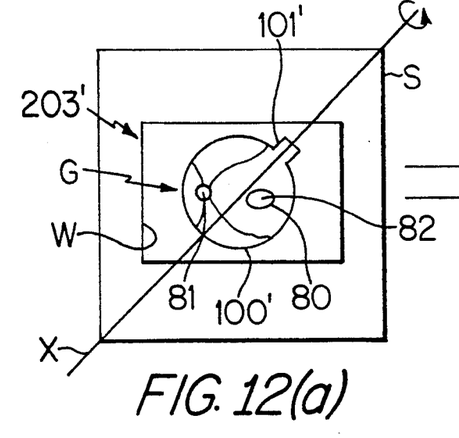
Figure 12B:
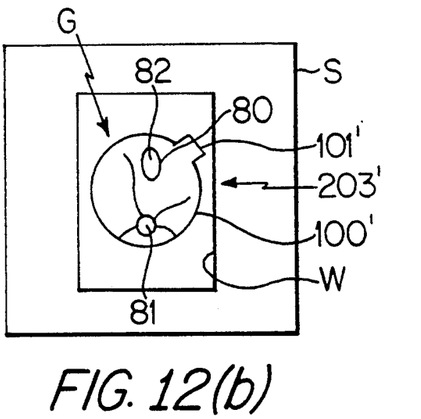

When using a mounted image 203' as shown in FIG. 12, the above procedure may not be sufficient to distinguish the front and back of the image. This is due to the fact that the mounting frame, i.e. the slide frame S, is square, and if the image is rotated around the diagonal X, it would be impossible to distinguish the front and back of an image having a notch situated at 45° to the horizontal.

Figure 13A:
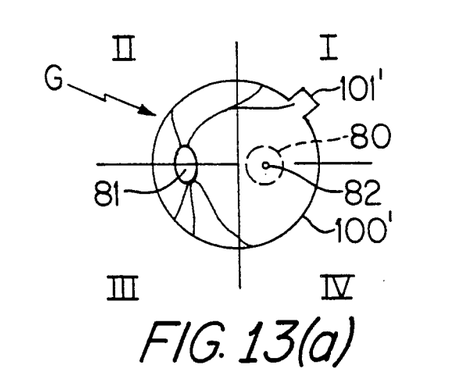
Figure 13B:
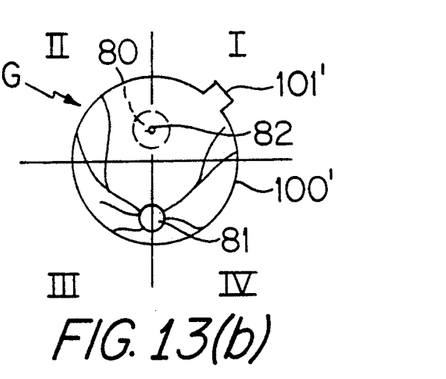

In such a case, front and back could however be distinguished by sampling points not only to the left and right but also top and bottom, and comparing the brightness in each of the quadrants I–IV as shown in FIG. 13(a), (b).

If for example the papilla and yellow striated area are situated in a substantially horizontal relationship to each other as shown in FIG. 13(a), the brightness of the quadrants (I) ~ (IV) follows the relation:

$$[(I)+(IV)]-[(II)+(III)] > [(I)+(II)]-[(III)+(IV)] \qquad (1).$$

Further if the papilla and yellow striated area are situated in a substantially vertical relationship to each other as shown in FIG. 13(b):

$$[(I)+(IV)]-[(II)+(III)] < [(I)+(II)]-[(III)+(IV)] \quad (2).$$

It is thus possible to know the orientation of the image.

Finally, image data is recorded on a high capacity recording apparatus 208 consisting of an optical disk or the like together with left/right eye identification data obtained as described hereintofore, and the subject's name, age and sex input by the operator from the keyboard 215 or from an external data base via the communications interface 211.

If a plurality of images of the same subject are taken and only specific images are to be filed, the data may also be temporarily stored in a disk apparatus. Recording supports such as optical disks or magneto-optic disks are interchangeable, and image data for at least 100 people can be stored on one support. In group health check ups, therefore, one recording support would be sufficient for one day's work, and the data could also be transferred to health centers and photographic locations. However in hospitals, when it is required to transfer only a very small amount of image data for a single examination of one patient, the use of a high capacity storage apparatus is often unnecessary. In such a case, a memory card of suitable capacity may be used as a recording support.

The image data is filed by means of a program of the CPU 212 stored in the disk apparatus 208. In this case, personal information about the subject and image data could be linked or cross-referenced by the following methods:

(1) Editing and storing personal data and image data in the same file.
(2) Storing personal data and image data in completely different files,
(3) Saving only a personal data file in the data base, the image data file name being specified in the personal data file.

The left and right eyes must be distinguished from one another for retrieval at a later date. This could be accomplished in each of the above methods as follows:

Method (1):
Data could be listed in the order: Personal data, left eye, right eye.

Method (2):
Data identifying the left eye and right eye could be attached to the file name.

Method (3):
A correspondance table for the left eye, right eye and image file could be constructed in the personal data file.

This filing apparatus and controlling software is easily implemented by a personal computer, hardware options and data base software.

TYPICAL APPLICATIONS OF THE EMBODIMENT (1) Image input to the frame memory 206 may be performed directly from the fundus camera GK or similar apparatus. There is then no need to distinguish front and back, and the apparatus is used only to identify the left and right eyes. In such a case, as described hereintofore, an area CCD P is disposed at the position of the film 14 of the fundus camera GK, and the signal from this CCD P is directly input to the frame memory 206.

Figure 18:
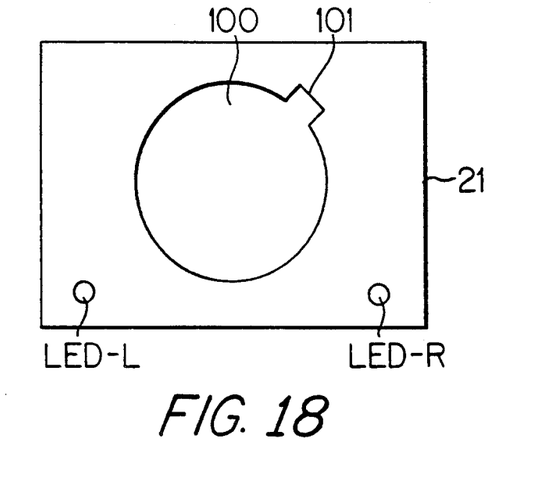
FIG. 18 is a schematic diagram illustrating another example of the mask shown in FIG. 1.
Figure 19:
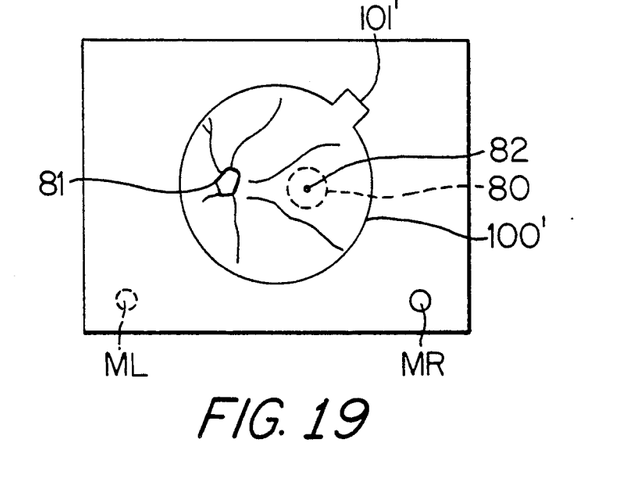
FIG. 19 is a schematic diagram of an image file using the mask of FIG. 18.
Figures 20A, 20B:
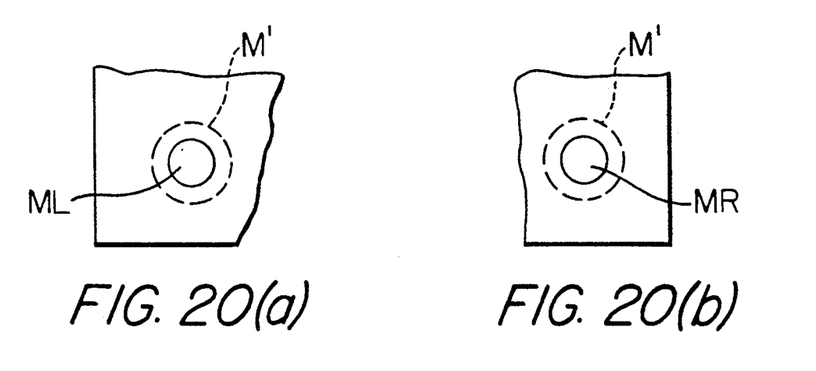

In this arrangement, as shown in FIG. 18, light emitting diodes LED-L, LED-R for left/right detection are also disposed in regions facing the area CCD P at the bottom left and right of the mask 21. When taking a photograph, either LED-L or LED-E is illuminated depending on whether the left or right eye is being examined, and a mark MR (or ML) for left/right identification by light and dark is added to the subject's image file recorded in the filing system PS (MR in FIG. 19). When image processing (filing or analysis) is performed, the central processing unit 212 performs left/right identification from the mark on the image stored in the frame memory 206 as described hereintofore. For this purpose, the central processing unit 212 scans addresses of the frame memory 208 corresponding to the regions where the marks MR, ML are recorded, and left or right eye identification is therefore very rapid. In this case, if the scanning range is set to be slightly larger than the size of the marks MR, ML as shown by the broken line M in FIG. 20(a), (b), left and right can be identified with precision even if there is some recording error in the address.

In the aforesaid embodiment, an assembly consisting of a fundus camera and filing system FS was described. It may however apply also to an assembly consisting of a slit lamp and filing system FS in order to photograph and record images of the cornea or front chamber or front portion of the subject's eye.

(2) A light amount histogram as shown in FIG. 4 may be calculated from image data, a slice level taken from only the notch of the field diaphragm 21 or the optic nerve papilla, and front/back and left/right identification performed by extracting salient features.

(3) If it detected that the original image has an incorrect orientation, the processor issues a warning, and simultaneously performs a coordinate transformation on the image so that the image is input with the correct orientation. The issue of a warning is not however absolutely indispensable each time this coordinate transformation is performed.

(4) For very poor images as those of eyes with cataracts, the automatic identification result can be overridden by input from the keyboard (manual correction).

(5) The following method may also be used to judge whether front and back have been reversed on a diagonal of an original image in a slide frame. This method is more accurate than that described in embodiment 1.

(1) Changing the position of the notch on the original image

Figure 14A:
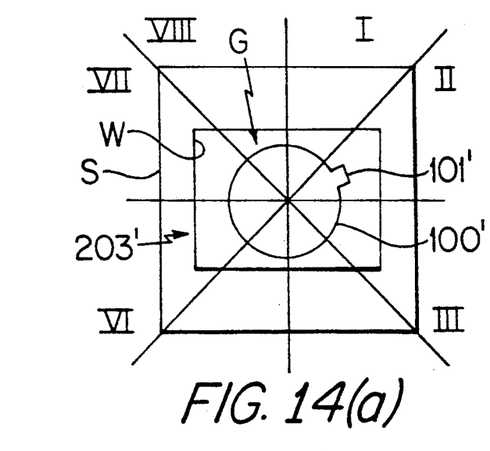
Figure 14B:
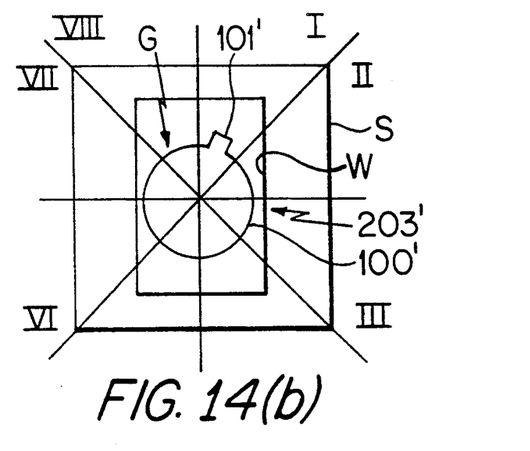

The notch is not positioned at an angle of 45°, but preferably at an angle of 22.5' from the horizontal on the field diaphragm of FIG. 2. In this case, the image is divided into eight sections I~VIII as shown in FIG. 14, and front/back can be identified. Notch detection is performed by the same method as that in embodiment 1. This method gives increased precision, but it is necessary to modify the fundus camera.

(2) Detecting the shape of the slide mount and method for distinguishing slide arranged condition A variable power lens is used for the lens 204. By detecting the shape of a frame window W in the mount (slide frame S), it is possible to determine whether the papilla and yellow striations or maoule luter are situated such that they are in a substantially horizontal relationship to each other.

Figure 15:
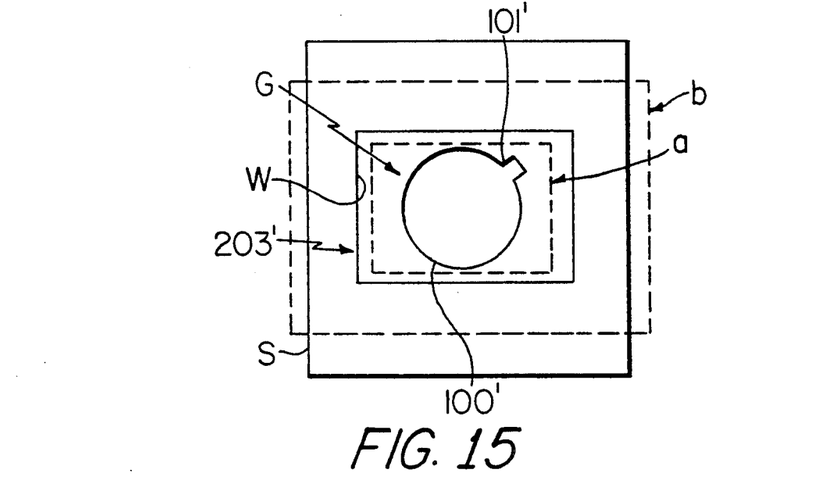
FIG. 15 and FIG. 16 are schematic diagrams illustrating one example of detecting the frame shape of a slide photograph.

To pick up an image, an area b including the slide frame S which is larger than the pickup area a is scanned as shown in FIG. 15. The position of the slide frame S is essentially fixed by the mount holder, so the position of the frame window W is also essentially fixed.

Figure 16:
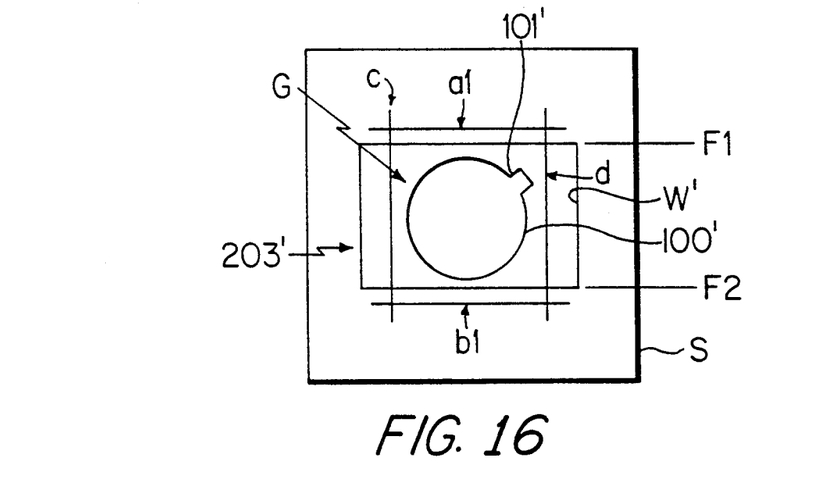

In this case, four lines can be drawn so as to form a square, i.e. lines a1, b1 parallel to the long side of the frame window W which do not cut it, and lines c, d parallel to the short side of the frame window W which do cut it, as shown in FIG. 16.

When the image is scanned by a spot illumination along the lines a1, b1, practically no variation of light amount is found.

Figure 17A:
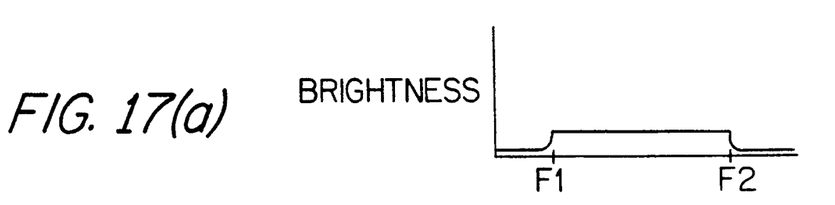
FIG. 17(a) and (b) are schematic diagrams showing the variation of the amount of light when the slide frame shape of FIG. 16 is scanned.
Figure 17B:
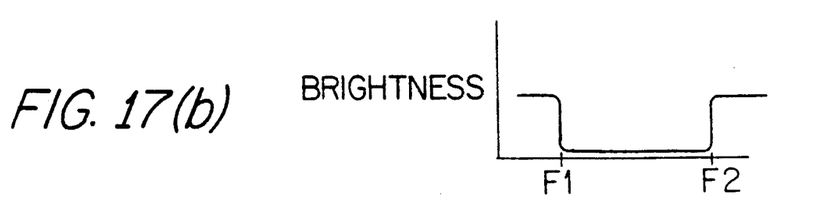

When the image is scanned by a spot illumination, along the lines c, d, however, a variation of light amount is found as is shown in FIG. 17(a) for the case of transmitted light, and FIG. 17(b) for the case of reflected light (the transmittance/reflectance in regions other than the image on the film is no greater than several percent, so reflection illumination is preferable).

If this light variation is detected, the orientation of the slide frame S can therefore be determined. Further, four lines have been shown in FIG. 16, but in principle two of the aforesaid lines which are mutually perpendicular may be used. The lens 204 may be a zoom lens or a variable power lens. In this case, processing is performed by the central processing unit. The frame may also be detected by a separate image pickup apparatus.

Further, in the aforesaid embodiment, the orientation in which the long and short sides of the slide frame S were set was identified from the light amount variation on the lines a1, b1, c, d. The embodiment is not however necessarily limited to this arrangement, it being possible to perform the same identification by for example scanning the square region enclosed by the lines a1, b1, c, d using a line illumination.

By combining the aforesaid mount shape detection method with the aforesaid method for detecting a notch or papilla, the front and back of the image can be identified and left/right eye identification can be performed.

As described hereinbefore, according to this invention, front/back, and left/right eye identification of input images is performed automatically. When the images are filed, therefore, problems caused by forgetting to specify or confusing the left or right eye are prevented. The method is also very well suited for inputting normal fundus images which are almost always obtained in group health examinations.

Further, if left and right or front and back are incorrectly input, a warning is issued to the operator, or image position data read by the photographic image reader is converted to correct image position data. The images are therefore read easily and accurately.

What is claimed is:

1. An ophthalmological image processor comprising:
   inputting means for inputting an electronic image of a subject's eye;
   display means for displaying the image input by said inputting means; and
   image identification/processing means for identifying at least one of whether said image is that of the left or right eye, whether said image is a front or back image, and whether said image is a top, bottom, left, or right image by the positions of light and dark regions on the image, and causing the result of this identification to be displayed by said display means.

2. An ophthalmological image processor as defined in claim 1 wherein said image inputting means is an image pickup means.

3. An ophthalmological image processor as defined in claim 2 wherein said image inputting means is a fundus camera.

4. An ophthalmological image processor as defined in claim 2 wherein said image inputting means is a video camera.

5. An ophthalmological image processor as defined in claim 1 wherein said image inputting means is a video camera installed at a certain height above a light box provided with a film holder.

6. An ophthalmological image processor as defined in claim 1 wherein said image inputting means is a magnetic disk apparatus.

7. An ophthalmological image processor as defined in claim 6 wherein said magnetic disk apparatus is a still video apparatus.

8. An ophthalmological image processor as defined in claim 6 wherein said magnetic disk apparatus is a magnetic card reader.

9. An ophthalmological image processor as defined in claim 6 wherein said magnetic disk apparatus is a read/write device which can record and reproduce said identification result together with a fundus image.

10. An ophthalmological image processor as defined in claim 1 characterized in that said image is identified as being that of either the left or right eye by determining whether the left or right half of the input image is brighter.

11. An ophthalmological image processor as defined in claim 1 wherein said identification means identifies the state of said image by considering the whole effective surface enclosed within the image of the subject's eye to be divided into a plurality of areas, and determining in which of said areas there is a region having a brightness greater than a predetermined reference level.

12. An ophthalmological image processor as defined in claim 11 characterized in that said identification means identifies whether said image is that of the left or right eye by determining whether regions having a brightness greater than said reference level are more numerous in a left or right area.

13. An ophthalmological image processor as defined in claim 1 characterized in that said image inputting means is a photographic image reader for reading a fundus photograph having a mark for identifying left, right, front and back,
   and said identifying means issues a warning to the operator if left, right, back or front of said fundus photograph are incorrectly input when the photograph is read by said photographic image reader.

14. An ophthalmological image processor as defined in claim 1 characterized in that said image inputting means is a photographic image reader for reading a fundus photograph having a mark for identifying left, right, front and back,
   and said identifying means performs a coordinate ransformation on incorrectly input image position data such that it is correctly input if left, right, back or front of said fundus photograph are incorrectly input when the photograph is read by said photographic image reader.

* * * * *

UNITED STATES PATENT AND TRADEMARK OFFICE
CERTIFICATE OF CORRECTION

PATENT NO. : 5,270,924
DATED : December 14, 1993
INVENTOR(S) : Masayuki Hideshima It is certified that error appears in the above-indentified patent and that said Letters Patent is hereby corrected as shown below:

Claim 11, column 10, line 39, change "arcas" to --areas--.

Claim 14, column 10, line 62, change "ransformation" to --transformation--.

Signed and Sealed this

Thirteenth Day of September, 1994

Attest:

Attesting Officer

BRUCE LEHMAN

Commissioner of Patents and Trademarks